United States Patent
Lee et al.

(10) Patent No.: US 10,364,468 B2
(45) Date of Patent: Jul. 30, 2019

(54) SYSTEMS AND METHODS FOR ANALYZING CIRCULATING TUMOR DNA

(71) Applicant: Seven Bridges Genomics Inc., Cambridge, MA (US)

(72) Inventors: Wan-Ping Lee, Somerville, MA (US); Devin Locke, Medford, MA (US)

(73) Assignee: Seven Bridges Genomics Inc., Cambridge, MA (US)

( * ) Notice: Subject to any disclaimer, the term of this patent is extended or adjusted under 35 U.S.C. 154(b) by 0 days.

(21) Appl. No.: 14/994,385

(22) Filed: Jan. 13, 2016

(65) Prior Publication Data
US 2017/0198351 A1    Jul. 13, 2017

(51) Int. Cl.
| G01N 33/48 | (2006.01) |
| G01N 33/50 | (2006.01) |
| C12Q 1/6886 | (2018.01) |
| G06F 19/12 | (2011.01) |
| G06F 19/22 | (2011.01) |

(52) U.S. Cl.
CPC ........... *C12Q 1/6886* (2013.01); *G06F 19/12* (2013.01); *G06F 19/22* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |

(Continued)

FOREIGN PATENT DOCUMENTS

| KR | 101282798 B1 | 7/2013 |
| WO | 2007/086935 A2 | 8/2007 |

(Continued)

OTHER PUBLICATIONS

Garber, 2011, Computational methods for transcriptome annotation and quantification using RNA-Seq, Nat Meth 8(6):469-477.

(Continued)

*Primary Examiner* — Russell S Negin

(74) *Attorney, Agent, or Firm* — Kip L. Bodi

(57) ABSTRACT

The invention provides oncogenomic methods for detecting tumors by identifying circulating tumor DNA. A patient-specific reference directed acyclic graph (DAG) represents known human genomic sequences and non-tumor DNA from the patient as well as known tumor-associated mutations. Sequence reads from cell-free plasma DNA from the patient are mapped to the patient-specific genomic reference graph. Any of the known tumor-associated mutations found in the reads and any de novo mutations found in the reads are reported as the patient's tumor mutation burden.

20 Claims, 12 Drawing Sheets

(56) References Cited

U.S. PATENT DOCUMENTS

| | | |
|---|---|---|
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,321,623 B2 | 1/2008 | Dambrackas |
| 7,483,585 B2 | 1/2009 | Brakus, Jr. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,972,201 B2 | 3/2015 | Mande et al. |
| 9,063,914 B2 | 6/2015 | Kural et al. |
| 9,092,402 B2 | 7/2015 | Kural et al. |
| 9,116,866 B2 | 8/2015 | Kural |
| 2002/0164629 A1 | 11/2002 | Quake et al. |
| 2002/0190663 A1 | 12/2002 | Rasmussen |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatrnan et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0003571 A1 | 1/2008 | McKeman et al. |
| 2008/0077607 A1* | 3/2008 | Gatawood ........... H03M 7/3084 |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Camevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0232480 A1 | 9/2013 | Winterfeldt et al. |
| 2013/0289099 A1 | 10/2013 | Goff et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Wesber et al. |
| 2014/0281708 A1 | 9/2014 | Adam et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0112602 A1 | 4/2015 | Kural et al. |
| 2015/0112658 A1 | 4/2015 | Kural et al. |
| 2015/0344970 A1 | 12/2015 | Vogelstein et al. |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015027050 A1 | 2/2015 |
| WO | 2015058093 A1 | 4/2015 |
| WO | 2015058095 A1 | 4/2015 |

OTHER PUBLICATIONS

Glusman, 2014, Whole-genome haplotyping approaches and genomic medicine, Genome Med 6:73.

Goto, 2010, BioRuby: bioinformatics software for the Ruby programming language, Bioinformatics 26(20):2617-2619.

Gotoh, 1982, An Improved Algorithm for Matching Biological Sequences, J Mol Biol 162:705-708.

Gotoh, 1999, Multiple sequence alignment: algorithms and applications, Adv Biophys 36:159-206.

Grabherr, 2011, Full-length transcriptome assembly from RNA-Seq data without a reference genome, Nat Biotech 29(7):644-654.

Guttman, 2010, Ab initio reconstruction of cell type-specific transcriptomes in mouse reveals the conserved multi-exonic structure of lincRNAs, Nat Biotech 28(5):503-510.

Guttman, 2010, Ab initio reconstruction of transcriptomes of pluripotent and lineage committed cells reveals gene structures of thousands of lincRNAs, NIH-PA Author Manuscript.

Haas, 2004, DAGchainer: a tool for mining segmental genome duplications and synteny, Bioinformatics 20(18):3643-3646.

Harenberg, 2014, Community detection in large-scale networks: a survey and empirical evaluation, WIREs Comp Stat 6:426-439.

Harrow, 2012, GENCODE: The reference human genome annotation for the ENCODE Project, Genome Res 22:1760-1774.

He, 2010, Optimal algorithms for haplotype assembly from whole-genome sequence data, Bioinformatics 26:i183-i190.

(56) References Cited

OTHER PUBLICATIONS

Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 30, 2014, for International Patent Application No. PCT/US14/58328, filed Sep. 30, 2014 (22 pages).
Interntional Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filed Jun. 10, 2016 (8 pages).
International Search Report and Written Opinion of the International Searching Authority dated Nov. 17, 2015 for International Application No. PCT/US2015/048891 (11 pages).
Kano, 2010, Text mining meets workflow: linking U-Compare with Taverna, Bioinformatics 26(19):2486-7.

Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao 2012, Why Workflows Break—Understanding and Combating Decay in Taverna Workflows, eScience 2012, Chicago, Oct. 2012.
Grasso, 2004, Combining partial order alignment and progressive multiple sequence alignment increases alignment speed and scalability to very large alignment problems, Bioinformatics 20(10):1546-1556.

(56) References Cited

OTHER PUBLICATIONS

Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, MOSAIK: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: A MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Posada, 1998, MODEL TEST: testing the model of DNA substitution, Bioinformatics 14(9):817-8.
Potter, 1994, ASC: An Associative-Computing Paradigm, Computer 27(11):19-25.

(56) References Cited

OTHER PUBLICATIONS

Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: An XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at https://cs.nyu.edu/mishra/PEOPLE/sun_bing.pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Newman et al., An ultrasensitive method for quantitating circulating tumor DNA with broad patient coverage. Nature Medicine. Apr. 6, 2014; vol. 20, No. 5; pp. 1-22.
Olsson et al., Serial monitoring of circulating tumor DNA in patients with primary breast cancer for detection of occult metastatic disease. EMBO Molecular Medicine. May 18, 2015; vol. 7, No. 8; pp. 1034-1047.
Written Opinion issued in PCT/US17/13329 dated Apr. 7, 2017.
The 1000 Genomes Project, 2015, A global reference for human genetic variation, Nature 526:68-74.
Li, 2010, A survey of sequence alignment algorithms for next-generation sequencing, Briefings in Bionformatics 11(5):473-483.
BCF2 Quick Reference (r198), available at http://samtools.github.io/hts-specs/BCFv2_qretpdf.
Durbin, 2014, Efficient haplotype matching and storage using the positional Burrows-Wheeler transform (PBWT), Bioinformatics 30(9):1266-1272.
Layer, 2015, Efficient genotype compression and analysis of large genetic-variation data sets, Nat Meth 13(1):63-65.
Layer, 2015, Efficient compression and analysis of large genetic variation datasets, Biorxiv preprint, available at http://biorxiv.org/content/early/2015/04/20/018259.
Li, 2015, BGT: efficient and flexible genotype query across many samples, arXiv:1506.08452 [q-bio.GN].
Li, 2015, Towards Better Understanding of Artificats in Variant Calling from High-Coverage Samples, arXiv:1404.0929 [q-bio.GN].
Popitsch, 2013, NGC: lossless and lossy compression of aligned high-throughput sequencing data, Nucl Acids Res, 41(1):e27.
Sudmant, 2015, An integrated map of structural variation in 2,504 human genomes, Nature 526:75-81.
Tewhey, 2011, The importance of phase information for human genomics, Nat Rev Gen 12:215-223.
The Variant Call Format (VCF) Version 4.2 Specification (Jan. 26, 2015), available at https://samtools.github.io/hts-specs/VCFv4.2.pdf.
Abouelhoda, 2012, Tavaxy: integrating Tavema and Galaxy workflows with cloud computing support, BMC Bioinformatics 13:77.
Agarwal, 2013, SINNET: Social Interaction Network Extractor from Text, Proc IJCNLP 33-36.

(56) References Cited

OTHER PUBLICATIONS

Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioinformatics 29(10)1250-1259.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12):e1000589.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Cartwright, DNA assembly with gaps (DAWG): simulating sequence evolution, 2005, pp. iii31-iii38, vol. 21, Oxford University Press.
Denoeud, 2004, Identification of polymorphic tandem repeats by direct comparison of genome sequence from different bacterial strains: a web-based resource, BMC Bioinformatics 5:4 pp. 1-12.
Golub, 1999, Molecular classification of cancer: class discovery and class prediction by gene expression monitoring, Science 286, pp. 531-537.
Koolen, 2008, Clinical and Molecular Delineation of the 17q21.31 Microdeletion Syndrome, J Med Gen 45(11):710-720.
Lupski, 2005, Genomic disorders: Molecular mechanisms for rearrangements and conveyed phenotypes, PLoS Genetics 1(6):e49.
Parks, 2015, Detecting non-allelic homologous recombination from high-throughput sequencing data, Genome Biol 16:17.

\* cited by examiner

```
Subject Report ctDNA @ time = t1 normalized      normalized
tumor-associated mutations    read count t0   read count t1
    ct.10398A>G                   12.1            12.1
    ct.6253T>C                     1.3            1.29 de novo mutations
    ct.198A>C                       .6             .59
    ct.953T>A                      2.1            2.0
    ct.766G>A                       0              .5
```

FIG. 11

SYSTEMS AND METHODS FOR ANALYZING CIRCULATING TUMOR DNA

TECHNICAL FIELD

The invention relates to oncogenomics and to the detection, monitoring, and treatment of tumors.

BACKGROUND

About 8 million people die of cancer each year according to the World Health Organization. Cancer is the uncontrolled growth of cells and can lead to malignant tumors that resist treatment, spread through the body, and potentially recur after removal. Early detection and vigilant monitoring are key to minimizing cancer's harm.

A lump in a patient may be biopsied to determine if it is a malignant tumor, but this only occurs after the lump has appeared. Some tumors, such as lung tumors, require difficult and painful biopsies in which a fine needle is inserted to the site of the tumor. A minimally-invasive procedure known as "liquid biopsy", which involves sequencing DNA from a patient's blood, promises to provide early detection.

Unfortunately, there are limits to the insights offered by a liquid biopsy. Sequence reads are generally analyzed by mapping them to a reference genome. Any difference between a sequence read and the reference is called as a mutation in the patient without regard to which should be considered the healthy genotype. The physician is left to search the literature to interpret the mutations found in the patient.

SUMMARY

Circulating tumor DNA is identified using sequence reads from a patient's cell-free plasma DNA. The sequence reads are mapped to a genomic graph that represents a diversity of human genotypes including the patient's own healthy, non-tumor genotype. The genomic graph is annotated to identify known tumor-associated mutations and thus provides a successful match, or "hit", on any sequence reads that include those known tumor-associated mutations. The patient's tumor-related mutation population is reported and includes those known tumor-associated mutations to which the sequence reads mapped. Where any of the sequence reads include de novo mutations relative to the patient's non-tumor genotype, those de novo mutations are included in the reported patient's tumor-related mutation population. Thus by mapping sequence reads from a patient's cell-free plasma DNA to an annotated reference graph that includes the patient's non-tumor genotype, systems and methods of the invention may be used to provide a report of the patient's tumor-related mutation population, which includes both known tumor-associated mutations and de novo mutations found in ctDNA in the patient.

The methods described herein may be used with patients known or suspected to have cancer, as a method of identifying causal variants in order to better target treatments and, with tests over time, for determining whether treatments have worked and what new mutations may have been selected for in treatment. Because DNA from all of a patient's tumors and tumor clones circulates in the bloodstream, ctDNA allows the clinician to obtain information on the population of tumor clones present in a patient, rather than just one particular clone or tumor. Additionally, systems and methods of the invention may be used to analyze sequence reads from a patient's cell-free plasma DNA to detect ctDNA as a means of screening for cancer by determining whether ctDNA (and thus, presumably, tumors) are present and tracking them over time.

At the core of the detection of ctDNA from sequence reads from a patient's cell-free plasma DNA is the use of the reference graph, such as a patient-specific reference graph or a patient-specific directed acyclic graph (DAG). The patient-specific genomic reference graph is used for mapping sequence reads. The patient-specific genomic reference graph contains a variety of genomic references including, for example, one or a plurality of human genomes as well as sequences from the patient's non-tumor tissue. Use of a DAG supports very fast analysis of very large numbers of sequence reads. Without the use of the patient-specific genomic reference graph, to make the number of pairwise alignment comparisons required to compare each of the potentially millions of sequence reads from an NGS instrument run to each segment of every included reference would be intractable in many settings. The patient-specific genomic reference graph is created by aligning the reference sequences to identify portions that match when aligned. Redundancy is eliminated by storing those portions as single objects in memory. The complete sequence of any one of the reference sequences is represented by connecting those objects in their genomic order and those connections may be implemented using pointers to physical locations in computer memory of adjacent objects. This allows operations such as searches, lookups, or alignments to be performed without having to refer to an extrinsic index as would be required in a traditional sequence database. That is, the index-free adjacency of the patient-specific genomic reference graph is particularly well-suited for the rapid and efficient detection of ctDNA from NGS sequence reads.

In certain aspects, the invention provides a method for analyzing tumor DNA. The method includes obtaining a patient-specific genomic reference graph that represents known human genomic sequences as well as non-tumor DNA from the patient. The patient-specific genomic reference graph includes objects in a tangible memory subsystem of a computer system, wherein matching homologous portions of the sequences are each represented by a single object. Preferably, the patient-specific genomic reference graph includes one or more known tumor-associated mutations and one or more patient mutations. The method includes aligning sequence reads—obtained by sequencing a sample containing cell-free plasma DNA from the patient—to the patient-specific genomic reference graph and providing a report that includes at least one mutation in the sequence reads relative to the patient-specific genomic reference graph revealed in the aligning step. The sequence reads may be obtained by sequencing the sample containing the cell-free plasma DNA from the patient. The sequence reads may be aligned to the patient-specific genomic reference graph by using a processor of the computer system to perform a multi-dimensional look-back operation to find a highest-scoring trace through a multi-dimensional matrix.

The report can identify a patient's tumor-related mutation population, e.g., any of the known tumor-associated mutations as well as any de novo mutations found in the sequence reads. The report may also describe what proportion of the sequence reads align to mutation-associated branches in the patient-specific genomic reference graph. Additionally or alternatively, the report may identify distinct clones present in a tumor in the patient. Similarly, the report may describe a novel driver mutation present in the cell-free plasma DNA from the patient. Methods of the invention may include adding the novel driver mutation to the one or more known tumor-associated mutations in the patient-specific genomic reference graph for subsequent uses.

In some embodiments, methods include building the patient-specific genomic reference graph by obtaining the known human genomic sequences, obtaining non-tumor sequences for the non-tumor DNA from the patient, and finding and deleting redundancies among matching, homologous portions of the known human genomic sequences and the non-tumor sequences, leaving the matching homologus portions. An object is created in the tangible memory subsystem for each of the matching homologous portions and connections are created between pairs of the objects to create the patient-specific genomic reference graph.

Methods of the invention may include aligning a second set of sequence reads to the patient-specific genomic reference graph and producing a second report that identifies a patient's second tumor-related mutation population at a time different from an initial time associated with the patient's tumor-related mutation population. The second report may compare the patient's second tumor-related mutation population to the patient's initial tumor-related mutation population.

In some embodiments, the objects of the patient-specific genomic reference graph include pointers to adjacent ones of the objects such that the objects are linked into paths to represent the plurality of known human genomic sequences, wherein each pointer identifies a physical location in the memory subsystem at which the adjacent object is stored. In certain embodiments, objects of the reference DAG comprise vertex objects connected by edge objects and an adjacency list for each vertex object and edge object, wherein the adjacency list for a vertex object or edge object lists the edge objects or vertex objects to which that vertex object or edge object is adjacent. In certain embodiments, the objects each include an adjacency list, wherein each entry in an adjacency list is a pointer to an adjacent object, wherein each pointer identifies a physical location in the memory subsystem at which the adjacent object is stored. In some embodiments, the patient-specific genomic reference graph uses index-free adjacency to link the objects into paths to represent the plurality of known human genomic sequences.

In related aspects, the invention provides a system for analyzing tumor DNA. The system includes one or more processors coupled to a memory subsystem. Stored in the memory subsystem is a patient-specific genomic reference graph representing known human genomic sequences as well as non-tumor DNA from a patient, wherein matching homologous portions of the sequences are each represented by a single one of a plurality of objects stored in the memory subsystem. The system also includes instructions executable by the processor to cause the system to align sequence reads from cell-free plasma DNA of the patient to the patient-specific genomic reference graph and provide a report that includes at least one mutation in the sequence reads relative to the patient-specific genomic reference graph revealed by the aligning step. Preferably, the patient-specific genomic reference graph includes one or more known tumor-associated mutations and one or more patient mutations. The report identifies a patient's tumor-related mutation population, e.g., any de novo mutations and any of the known tumor-associated mutations found in the sequence reads. Optionally, the report further may identify any of: what portion of the sequence reads align to mutation-associated branches in the patient-specific genomic reference graph; a first clone and a second clone present in a tumor in the patient; and a novel driver mutation present in the cell-free plasma DNA from the patient. In some embodiments, the system is operable to build the patient-specific genomic reference graph by obtaining the known human genomic sequences; obtaining non-tumor sequences for the non-tumor DNA from the patient; finding and deleting redundancies among homologous portions of the known human genomic sequences and the non-tumor sequences, leaving the matching homologous portions; creating one of the objects in the tangible memory subsystem for each of the matching homologous portions; and creating connections between pairs of the objects to create the patient-specific genomic reference graph. In some embodiments, the objects of the patient-specific genomic reference graph include pointers to adjacent ones of the objects such that the objects are linked into paths to represent the plurality of known human genomic sequences, wherein each pointer identifies a physical location in the memory subsystem at which the adjacent object is stored. In certain embodiments, objects of the reference DAG comprise vertex objects connected by edge objects and an adjacency list for each vertex object and edge object, wherein the adjacency list for a vertex object or edge object lists the edge objects or vertex objects to which that vertex object or edge object is adjacent. In certain embodiments, the objects each include an adjacency list, wherein each entry in an adjacency list is a pointer to an adjacent object, wherein each pointer identifies a physical location in the memory subsystem at which the adjacent object is stored. In some embodiments, the patient-specific genomic reference graph uses index-free adjacency to link the objects into paths to represent the plurality of known human genomic sequences.

BRIEF DESCRIPTION OF THE DRAWINGS

FIG. 9 shows the matrices that represent the comparison.

FIG. 11 shows a report of what portion of the sequence reads align to DAG branches.

DETAILED DESCRIPTION

Figure 1:
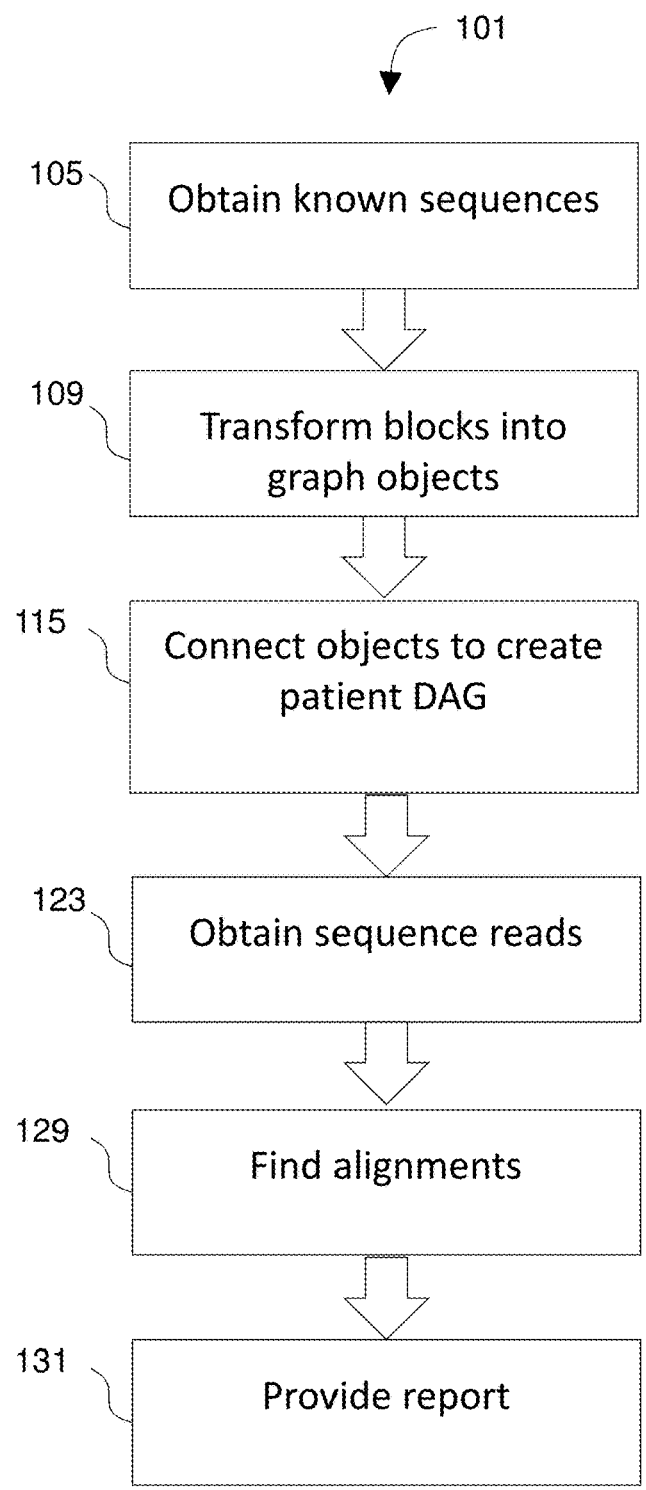
FIG. 1 diagrams a method for analyzing tumor DNA.

Systems and methods of the invention avoid the hassle and expense of biopsying tumors by instead operating with sequences from cell-free fragments of tumor DNA circulating in the bloodstream, known as circulating tumor DNA, or ctDNA. Genomic studies show that virtually all cancer tumors are associated with somatic genetic mutations, some of which rarely occur in healthy cells and thus provide specific tumor biomarkers. Tumor biomarkers can be assessed by looking at ctDNA. Liquid biopsies can provide temporal measurements of the total tumor burden as well as identify specific mutations that arise during therapy. Cancer may be detected or monitored by analyzing sequence reads obtained, for example, by sequencing a patient sample that includes the ctDNA. The sequence reads are analyzed by mapping them to a genomic reference that includes normal, non-tumor genetic sequence from the patient. Moreover, the reference is a patient-specific reference graph, such as a patient directed acyclic graph (DAG) that also includes any other known human reference sequences of interest that are available for inclusion. For example, the patient-specific genomic reference graph may include one or more published human genomes (e.g., hg18) and sequences obtained by sequencing the patient's healthy, non-tumor tissue.

The patient-specific genomic reference graph efficiently stores the reference sequences because matching, homologous portions of the reference sequences are represented using only a single object to eliminate redundancy. The patient-specific genomic reference graph supports very fast analysis commensurate with the pace at which data is generated by next-generation sequencing (NGS) technologies, because the objects in the DAG are stored and accessed using spatial memory addressing. Use of the patient-specific genomic reference graph provides results that are more accurate than other methods because each of the sequence reads is analyzed by simultaneously comparing it to the full range of known genetic variation, which avoids misleading inferences that arise when mapping a sequence read to a linear reference. Due to those benefits, mapping the ctDNA sequence reads to the patient-specific genomic reference graph allows tumor mutations to be identified rapidly and accurately.

In addition to allowing for non-invasive sampling, because DNA from all of a patient's tumors and tumor clones is circulating in the bloodstream, ctDNA allows the clinician to obtain information on the population of tumor clones present in a patient, rather than just one particular clone or tumor. Besides describing tumor clones in a patient, methods of the invention may be used in the sequencing of cell-free plasma DNA to detect ctDNA as a means of screening for cancer. See Newman et al., 2014, An ultra-sensitive method for quantitating circulating tumor DNA with broad patient coverage, Nat Med. 20(5):548-554, incorporated by reference.

Systems and methods of the invention address the challenge of separating ctDNA from other cell-free plasma DNA (DNA circulating in the blood plasma and not contained within cells). With prior art approaches, ctDNA is identified as such when known cancer-associated mutations are identified while ctDNA not containing any known cancer-associated mutations may be missed.

Systems and methods of the invention may be used with patients known to have cancer, for identifying causal variants in order to better target treatments and, with tests over time, for determining whether treatments have worked and what new mutations may have been selected for in treatment. Systems and methods of the invention may also be used with patients who are simply being screened for cancer, e.g., for determining whether ctDNA (and thus, presumably, tumors) are present and tracking them over time.

FIG. 1 diagrams a method 101 for analyzing tumor DNA. The method includes obtaining 105 known human genomic sequences as well as sequences from non-tumor DNA from the patient. Portions of the sequences that match each other when aligned are inferred to be homologous and identified as blocks that are transformed 109 into objects that are stored in a tangible memory device. The objects are connected 115 by edges to create a patient-specific genomic reference graph such that there is a path through the patient-specific genomic reference graph for each of the original known human genomic sequences as well as a path or paths for the non-tumor DNA from the patient.

Method 101 further includes obtaining 123 sequence reads from a sample containing cell-free plasma DNA from the patient and finding 129 alignments between the sequence reads and the patient-specific genomic reference graph. A report is provided 131 that includes at least one mutation in the sequence reads relative to the patient's non-tumor DNA revealed in the aligning step. The report may identify any mutation found in the sequence reads (i.e., novel to that patient) and any of the known tumor-associated mutations that are found in the sequence reads as the patient's tumor-related mutation population.

Figure 2:
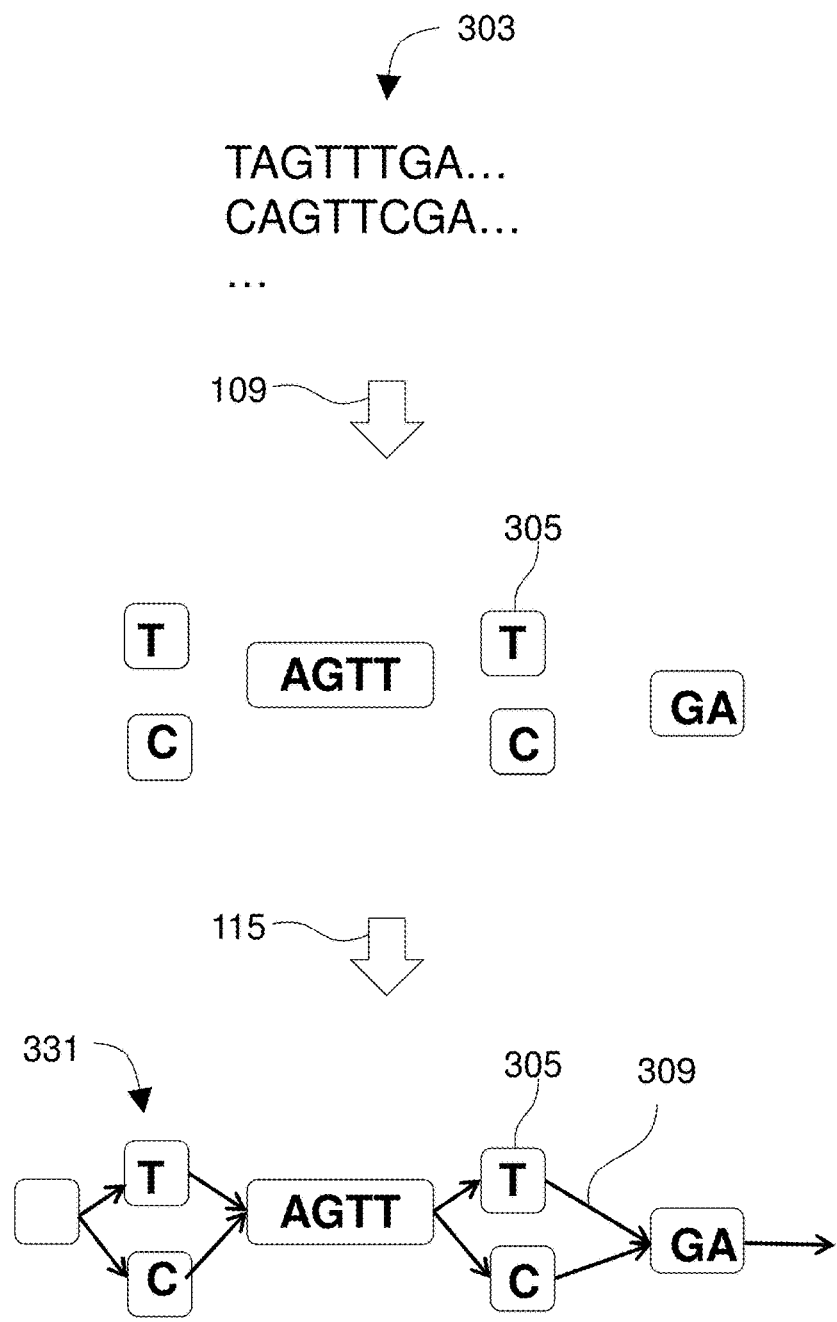
FIG. 2 shows the creation of a patient-specific genomic reference graph.

FIG. 2 shows the creation of a patient-specific genomic reference graph 331 from known human genomic sequences as well as non-tumor sequences from the patient. The known sequences 303—which include the known human genomic sequences as well as non-tumor DNA from the patient—are transformed into a graph 331 that includes vertex objects 305 and edge objects 309. Each of the sequences 303 are aligned to the others and in some embodiments, a multiple sequence alignment is performed. Portions of the sequences that match each other when aligned are identified as blocks and those blocks are transformed 109 into objects 205 that are stored in a tangible memory device. This results in finding and deleting redundancies among homologous portions of the known human genomic sequences and the nontumor sequences, leaving the matching homologous portions. Transforming those blocks into objects is done by creating one of the objects in the tangible memory subsystem for each of the blocks. The computer is used to create connections between pairs of the objects to create the patient-specific genomic reference graph.

In the fragments of sequence represented in FIG. 2, it can be seen that bases 2-5 of first sequence align to, and match, bases 2-5 of the second sequence. Thus those segments of those two sequences are identified as a block and systems of the invention create an object 305 to represent that AGTT string. It is noted that this object could potentially be stored using one byte of information. For example, if A=00, C=01, G=10, and T=11, then this block contains 00101111 (one byte). Where the original sequences 303 contain a very large number of reference sequences, the described methods provide a consider improvement to the operation of the computer system in comparison to a prior art method that stores an entire multiple sequence alignment.

The objects 305 are connected 115 to create paths such that there is a path for each of the original known sequences 303. The paths are directed and preferably in the sense that the direction of each path corresponds to the 5' to 3' directionality of the sequences. Further, the graph is acyclic in that no cycles are allowed due to the directionality of the paths. However, in certain embodiments, the paths may lack an associated directionality component, and some paths may be acyclic. The connections creating the paths can themselves be implemented as objects so that the blocks are represented by vertex objects 305 and the connections are represented by edge objects 309. Thus the directed graph comprises vertex and edge objects stored in the tangible memory device. The directed graph 331 represents the plurality of known sequences 303 in that each one of the original sequences can be retrieved by reading a path in the direction of that path. However, the directed graph 331 is a different article that the original sequences 303, at least in that portions of the sequences that match each other when aligned have been transformed into single objects 303. Thus if the original article includes hundreds or more complete human genomes, then billions of characters of information from the original article are transformed into a graph that uses much less disk space than if stored as, e.g., a multiple sequence alignment. It should be noted that in the figures, the patient-specific genomic reference graph is represented using only a few nodes and edges and a few nucleotide characters whereas in actual implementation, the DAG will be much larger than what is depicted here and too large to be represented in such figures. The patient-specific genomic reference graph 331 is preferably annotated to include one or more known tumor-associated mutations and one or more patient mutations.

One approach to building the patient-specific genomic reference graph is to first build a human reference DAG incorporating known human reference sequences and variants. Then, sequence reads from a sample of the patient's normal (non-tumor) DNA are aligned to that human reference DAG. The patient-specific ctDNA-detection reference DAG, or patient-specific genomic reference graph, is then built by incorporating any de novo mutations found using that first alignment step along with known tumor-associated mutations into the reference DAG.

Figure 3:
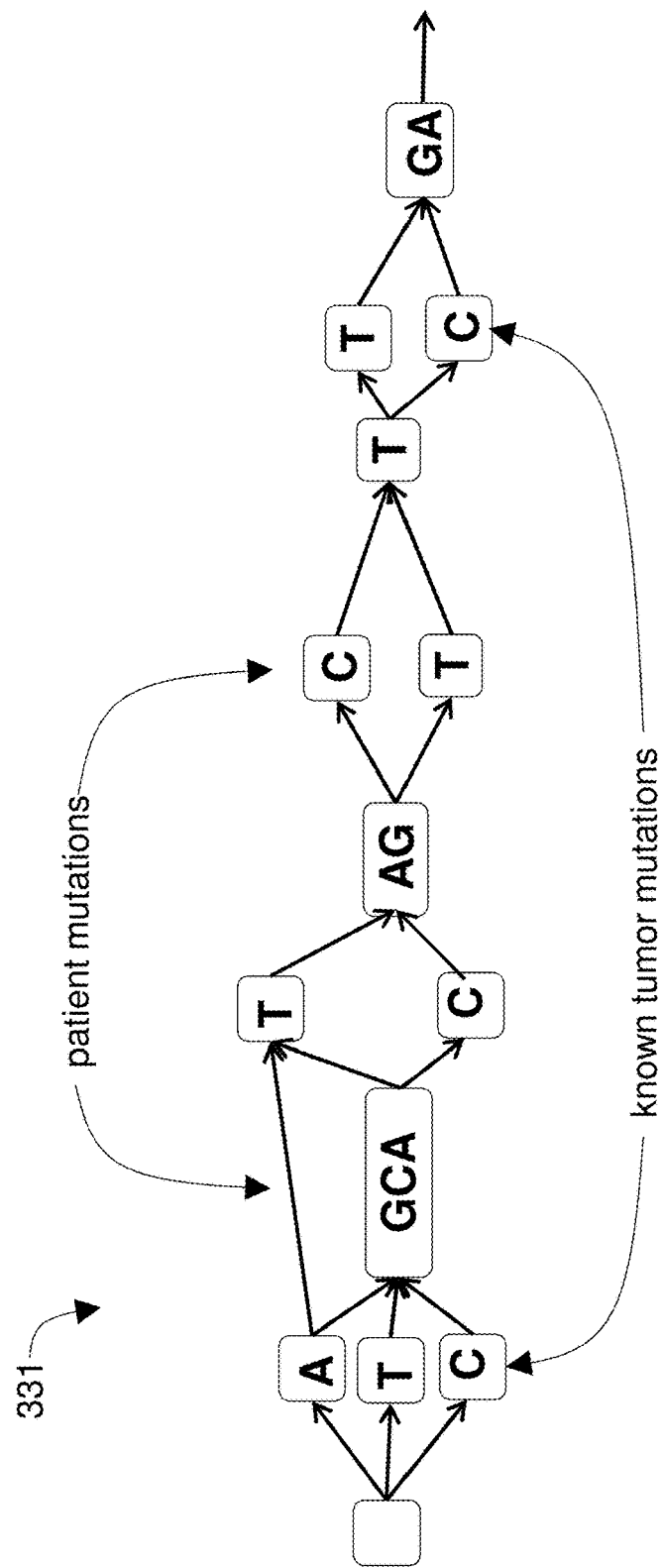
FIG. 3 shows known tumor mutations and patient mutations on the patient-specific genomic reference graph.

FIG. 3 shows known tumor mutations and patient mutations on the patient-specific genomic reference graph. Sequence reads from a patient sample containing ctDNA are aligned to the patient-specific genomic reference graph to report all known tumor-related mutations (if any) that those sequence reads successfully align to, along with any new de novo mutations identified, together with a proportion of reads aligned to each mutation branch preferably normalized for total number of reads aligning at that position. This may be taken as the patient's tumor-related mutation population at t0, e.g., as an initial assessment of clonality.

It may be desirable to, at a later point in time (e.g., in the treatment scenario after treatment has had time to take effect; in the screening scenario after a reasonable time has passed such that screening again makes sense), align a new set of reads from a newly-sequenced sample of the patient's cell-free plasma DNA to the patient-specific genomic reference graph. Then systems and methods of the invention may be used to report all tumor-related mutations that reads are aligned to together with proportion aligned, e.g., as the patient's tumor-related mutation population at t1, along with a comparison of this population of mutations to the previous round of testing.

Preferably, the alignment and reporting steps are performed by one or more processors of a computer system wherein the patient-specific genomic reference graph is stored within a non-transitory, tangible memory subsystem.

Figure 4:
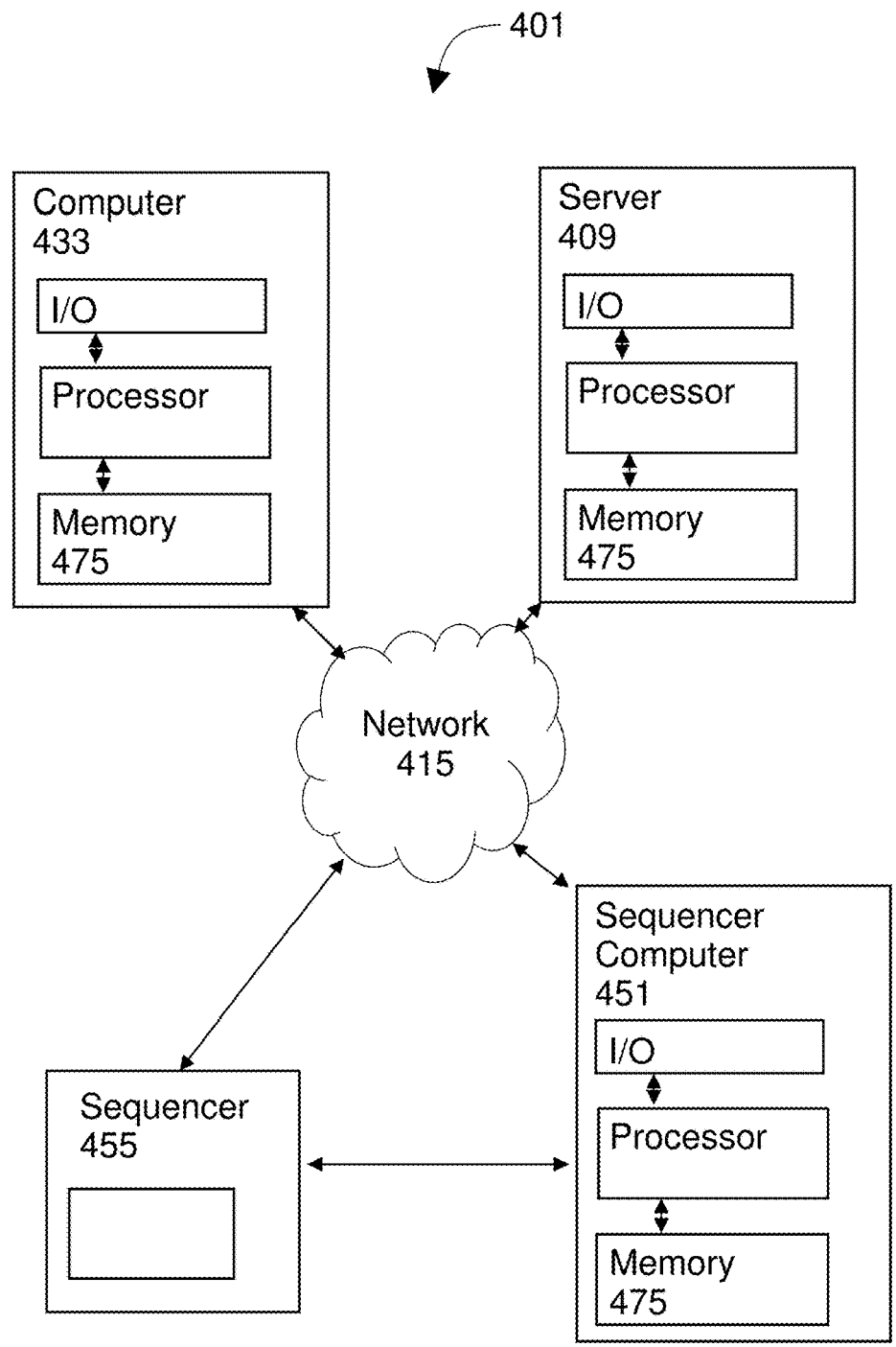
FIG. 4 diagrams a system of the invention.

FIG. 4 diagrams a system of the invention. The system 401 may be used to perform methods of the invention. The system 401 includes at least one computer 433. Optionally, the system 401 may further include one or more of a server computer 409 and a sequencer 455, which may be coupled to a sequencer computer 451. Each computer in the system 401 includes a processor coupled to a memory device and at least one input/output device. Thus the system 401 includes at least one processor coupled to a memory subsystem (e.g., a memory device or collection of memory devices 475). Using those mechanical components, the system 401 is operable to obtain a sequence generated by sequencing nucleic acid from a genome of a patient. The system uses the processor to transform the sequence 303 into the graph 331.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 475 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 401 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the graph is stored in the memory subsystem using adjacency lists, which may include pointers to identify a physical location in the memory subsystem 475 where each vertex is stored. In a preferred embodiment, the graph is stored in the memory subsystem 475 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Figure 5:
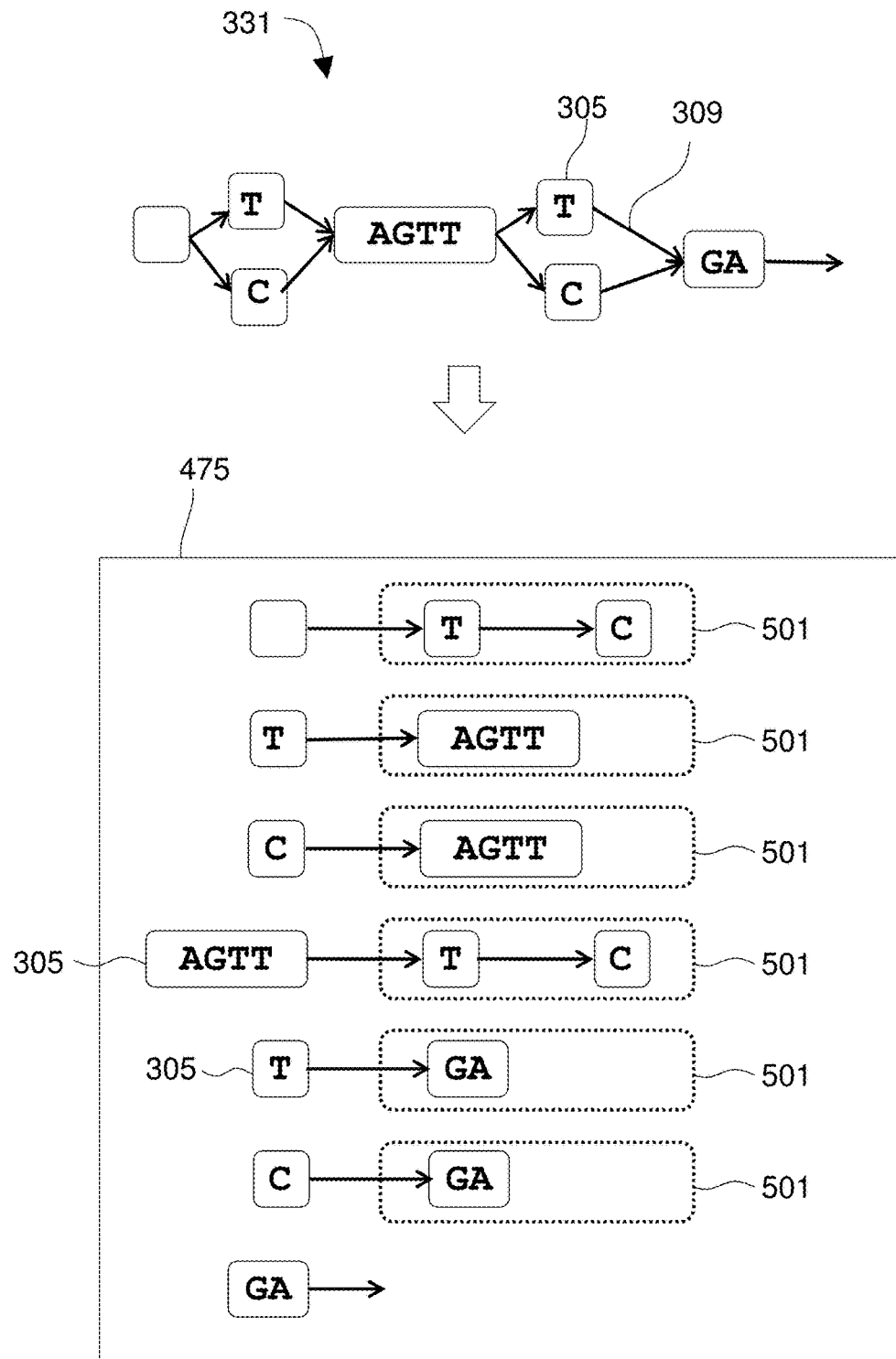
FIG. 5 shows the use of adjacency lists.

FIG. 5 shows the use of adjacency lists. An adjacency list 501 is used for each vertex 305. The system 401 uses a processor to create a graph 331 that includes vertex objects 305 and edge objects 309 through the use of adjacency, i.e., adjacency lists or index free adjacency. Thus, the processor may create the graph 331 using index-free adjacency wherein a vertex 305 includes a pointer to another vertex 305 to which it is connected and the pointer identifies a physical location in on a memory device 475 where the connected vertex is stored. The graph 331 may be implemented using adjacency lists such that each vertex or edge stores a list of such objects that it is adjacent to. Each adjacency list comprises pointers to specific physical locations within a memory device for the adjacent objects.

In the top part of FIG. 5, the graph 331 is illustrated in a cartoon-like visual-friendly format. The graph 331 will typically be stored on a physical device of memory subsystem 475 in a fashion that provide for very rapid traversals. In that sense, the bottom portion of FIG. 5 is not cartoon-like and represents that objects are stored at specific physical locations on a tangible part of the memory subsystem 475. Each node 305 is stored at a physical location, the location of which is referenced by a pointer in any adjacency list 501 that references that node. Each node 305 has an adjacency list 501 that includes every adjacent node in the graph 331. The entries in the list 501 are pointers to the adjacent nodes.

In certain embodiments, there is an adjacency list for each vertex and edge and the adjacency list for a vertex or edge lists the edges or vertices to which that vertex or edge is adjacent.

Figure 6:
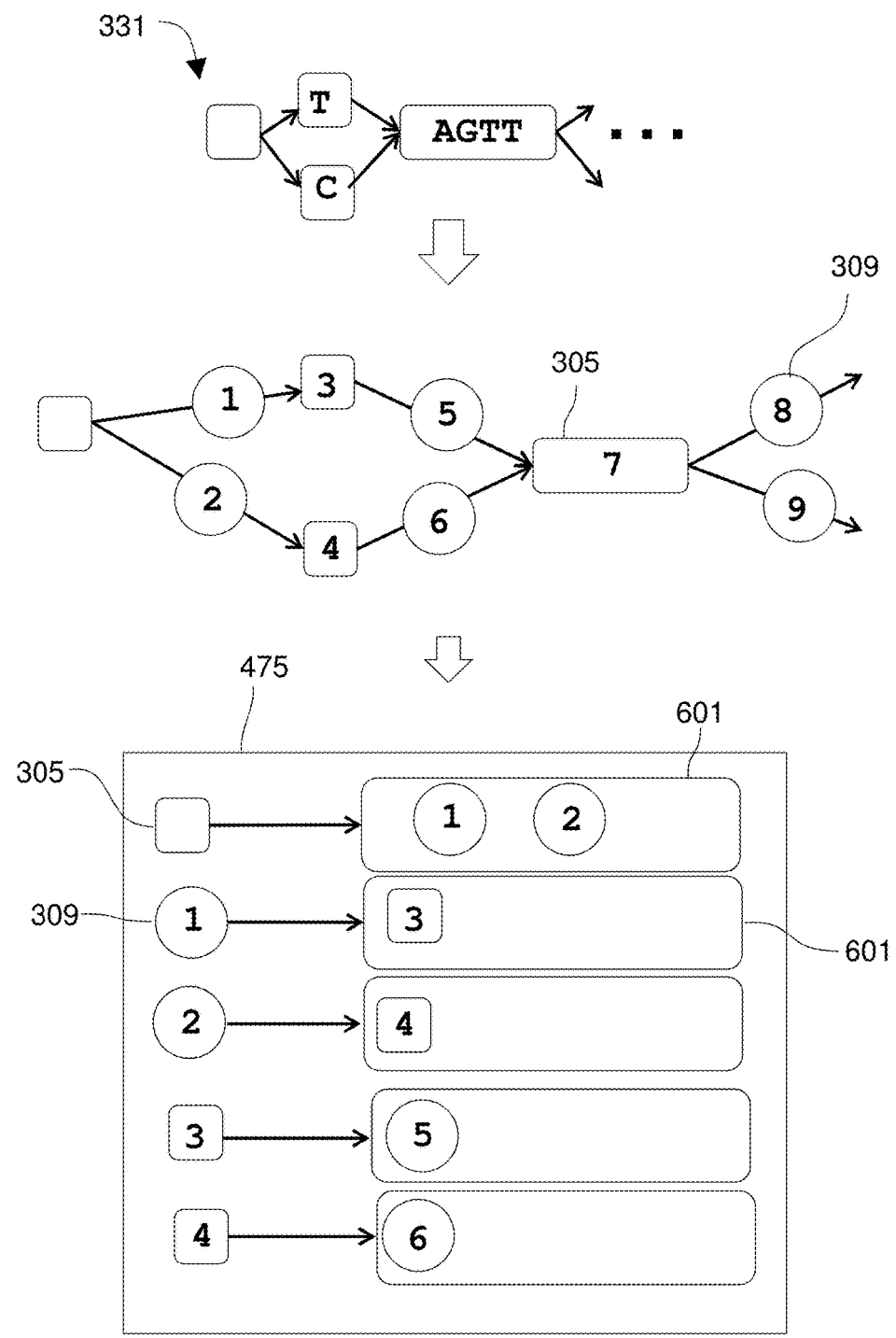
FIG. 6 shows adjacency lists where vertices and edges are stored as objects.

FIG. 6 shows adjacency lists where vertices and edges are stored as objects. An adjacency list 601 is used for each vertex 305 and edge 309. As shown in FIG. 6, system 401 creates the graph 331 using an adjacency list 601 for each vertex and edge, wherein the adjacency list 601 for a vertex 305 or edge 309 lists the edges or vertices to which that vertex or edge is adjacent. Each entry in adjacency list 601 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows a sequence to be queried against a large-scale genomic reference graph 331 representing millions or billions of bases, using a computer system 401. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale graph (i.e., a graph 331 that represents all loci in a substantial portion of the subject's genome). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a patient-specific genomic reference graph, FIGS. 5 and 6 are presented to illustrate useful formats. With reference back to FIG. 1, it is noted that methods of the invention use the patient-specific genomic reference graph with tumor sequence reads that are obtained from the patient. In some embodiments, sequence reads are obtained as an electronic article, e.g., uploaded, emailed, or FTP transferred from a lab to system 401. In certain embodiments, sequence reads are obtained by sequencing.

Figure 7:
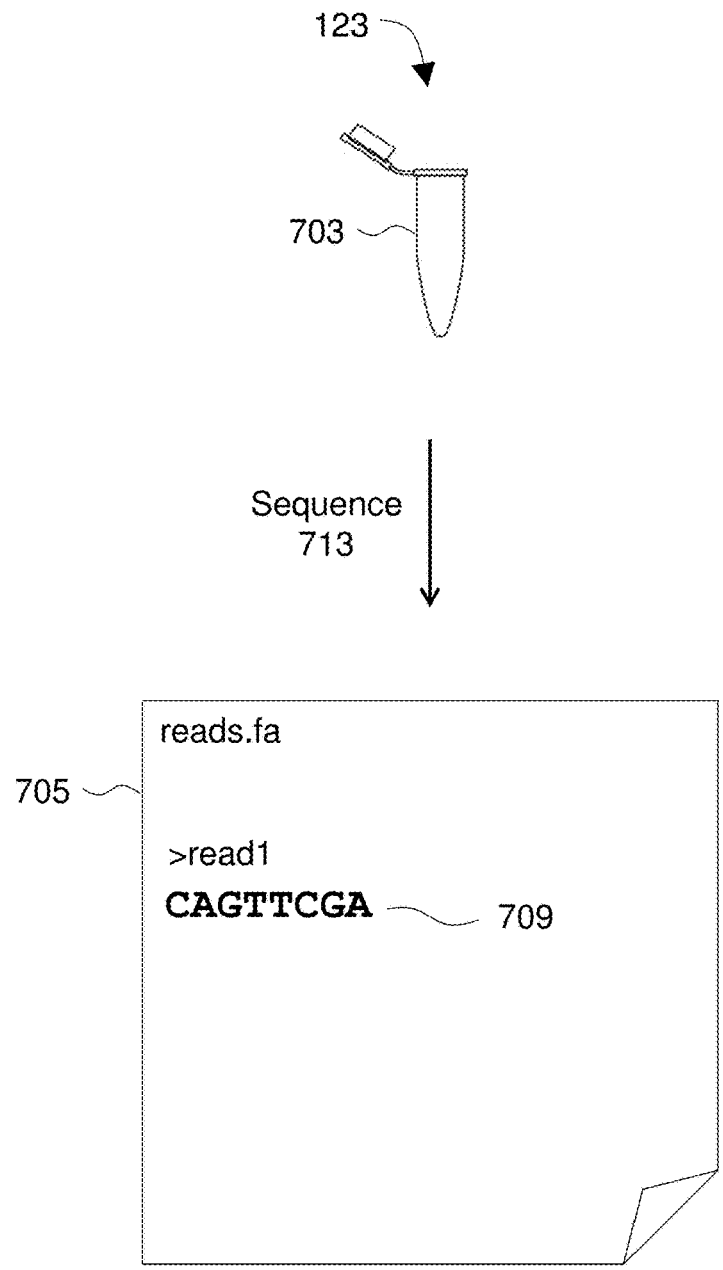
FIG. 7 illustrates obtaining sequence reads from a sample.

FIG. 7 illustrates obtaining sequence reads 705 from a sample 703. The illustrated steps may be applicable to either or both of obtaining sequences of the non-tumor DNA from the patient or obtaining sequence reads from a cell-free plasma DNA from a sample from the patient. For non-tumor DNA reads, a tissue sample may be obtained. For cell-free plasma DNA reads, a blood sample may be obtained from the patient and cell-free plasma DNA (cfDNA) may be isolated. Any suitable method may be used to isolate cfDNA and it may be preferable to use a commercially-available kit such as the circulating nucleic acid kit sold under the trademark QIAAMP by Qiagen (Venlo, Netherlands) or the plasma/serum cell-free circulating DNA purification mini kit sold by Norgen Biotek Corp. (Ontario, Canada). After isolation, sample 703 includes cell-free plasma DNA in a form amenable to sequencing, e.g., by next-generation sequencing (NGS) instruments.

In certain embodiments, sequence reads are obtained by performing sequencing 713 on a sample 703 from a subject. Sequencing may be by any method known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. No. 5,583,024; U.S. Pat. No. 5,674,713; and U.S. Pat. No. 5,700,673, the contents of which are incorporated by reference herein in their entirety. 454 sequencing involves two steps. In the first step of those systems, DNA is sheared into blunt-end fragments attached to DNA capture beads and then amplified in droplets. In the second step, pyrosequencing is performed on each DNA fragment in parallel. Addition of one or more nucleotides generates a light signal that is recorded by a CCD camera in a sequencing instrument.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. No. 7,960,120, U.S. Pat. No. 7,835,871, U.S. Pat. No. 7,232,656, U.S. Pat. No. 7,598,035, U.S. Pat. No. 6,306,597, U.S. Pat. No. 6,210,891, U.S. Pat. No. 6,828,100, U.S. Pat. No. 6,833,246, and U.S. Pat. No. 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 7, sequencing 713 generates a plurality of reads 705. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 105 in a format such as FASTA, FASTQ, or similar.

The sequence reads from the cell-free plasma DNA are aligned to the patient-specific genomic reference graph. Since the patient-specific genomic reference graph includes non-tumor sequences from the patient, any difference between the sequence reads from the cell-free plasma DNA and the patient-specific genomic reference graph, or de novo mutation, is presumptively a tumor-associated mutation.

Figure 8:
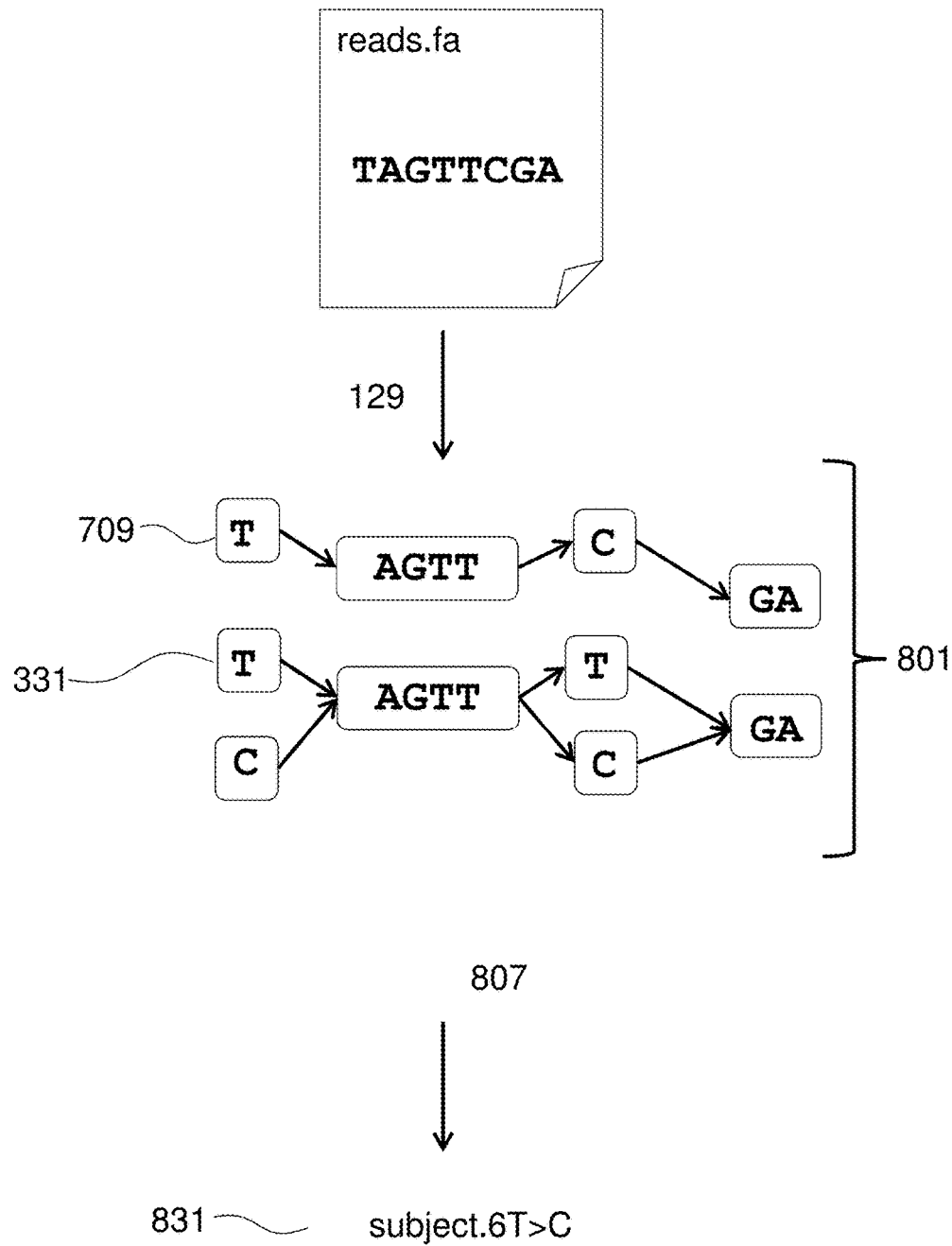
FIG. 8 illustrates aligning sequence reads to a patient-specific genomic reference graph.

FIG. 8 illustrates aligning sequence reads to a patient-specific genomic reference graph. The computer system may be used to find 129 alignments 801 between a sequence read 709 and the graph 331. Using alignment operations of the invention, reads can be rapidly mapped to a graph despite their large numbers or short lengths. Numerous benefits obtain by using a graph as a reference. For example, aligning against a graph is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference graph is provided here as an extension of pairwise alignment methods.

Pairwise alignment generally involves placing one sequence along part of target, introducing gaps according to an algorithm, scoring how well the two sequences match, and preferably repeating for various positions along the reference. The best-scoring match is deemed to be the alignment and represents an inference of homology between alignment portions of the sequences. In some embodiments, scoring an alignment of a pair of nucleic acid sequences involves setting values for the scores of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affect the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i)|x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, $B(i,i)=1$ and $0<B(i,j)[\text{for } i\neq j]<1$ is one possible scoring system. For instance, where a transition is thought to be more biologically probable than a transversion, matrix B could include $B(C,T)=.7$ and $B(A,T)=.3$, or other values desired or determined by methods known in the art.

A pairwise alignment, generally, involves—for sequence Q (query) having m characters and a reference genome T (target) of n characters—finding and evaluating possible local alignments between Q and T. For any 1≤i≤n and 1≤j≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_01 = 0 \text{ (for } 0 \le k \le n \text{ and } 0 \le l \le m)$$

$$H\_ij = \max\{H\_(i-1,j-1) + s(a\_i, b\_j), H\_(i-1,j) - W\_\text{in}, H\_(ij-1) - W\_\text{del}, 0\} \text{ (for } 1 \le i \le n \text{ and } 1 \le j \le m) \quad (1)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi, j−1) was used to compute the final maximum value for each cell. The backtracking stops when a zero is reached. The optimal-scoring alignment may contain greater than the minimum-possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 < j \le m, \ 0 < k \le n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \text{MISMATCH\_PEN, if } S[j] \ne A[k] = \max(p[j-1,k-1], i[j-1,k-1], d[j-1,k-1]) + \text{MATCH\_BONUS, if } S[j] = A[k] \quad (3)$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through the graph 331. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a graph 331 with the use of spatial memory addresses (e.g., native pointers or index-free adjacency) improves what the computer system is capable of, facilitating whole genomic scale analysis and epigenetic profiling to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[0], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d]=\max\{a,i,e,0\} \quad (6)$$

where
$e=\max\{M[j, p^*]+DELETE\_PEN\}$ for $p^*$ in P[d]
$i=M[j-1, d]+INSERT\_PEN$
$a=\max\{M[j-1,p^*]+MATCH\_SCORE\}$ for $p^*$ in P[d], if S[j]=d;
$\max\{M[j-1, p^*]+MISMATCH\_PEN\}$ for $p^*$ in P[d], if S[j]≠d As described above, e is the highest of the alignments of the first j characters of S with the portions of the graph up to, but not including, d, plus an additional DELETE_PEN. Accordingly, if d is not the first letter of the sequence of the node, then there is only one predecessor, p, and the alignment score of the first j characters of S with the graph (up-to-and-including p) is equivalent to M[j,p]+DELETE_PEN. In the instance where d is the first letter of the sequence of its node, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for the sequence 709 by calculating not only the insertion, deletion, and match scores for that element, but looking backward (against the direction of the graph) to any prior nodes on the graph to find a maximum score.

Figure 9:
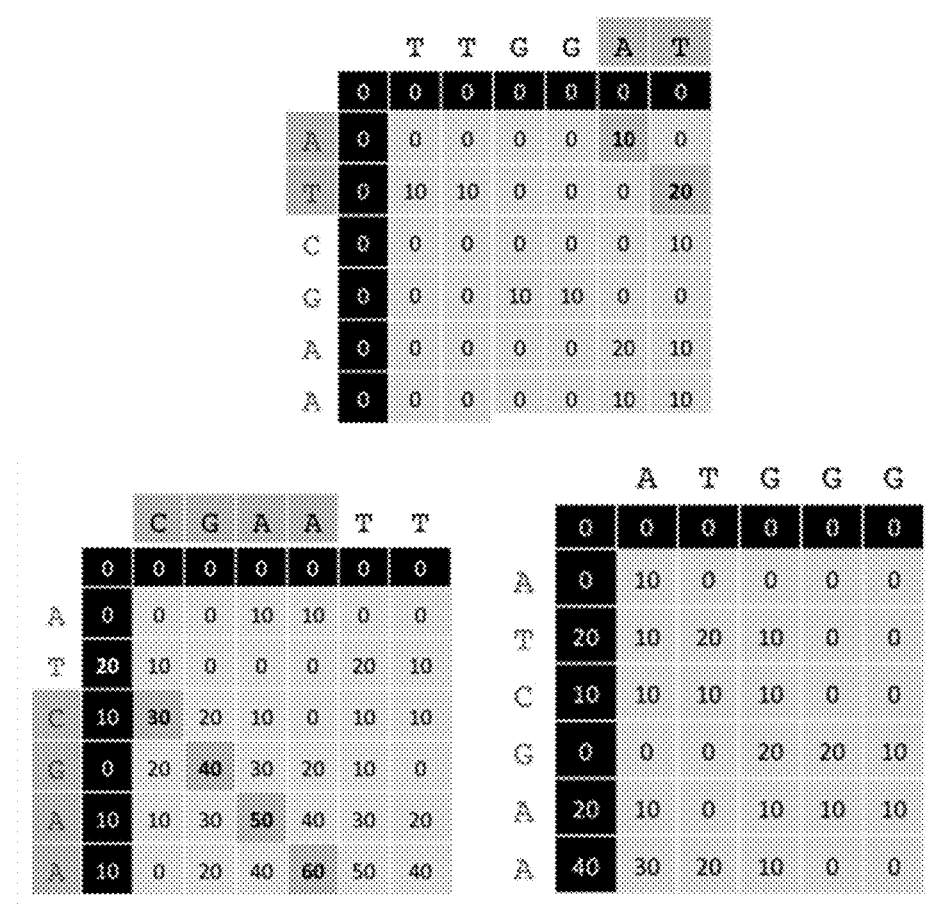

FIG. 9 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99, incorporated by reference.

Figure 10:
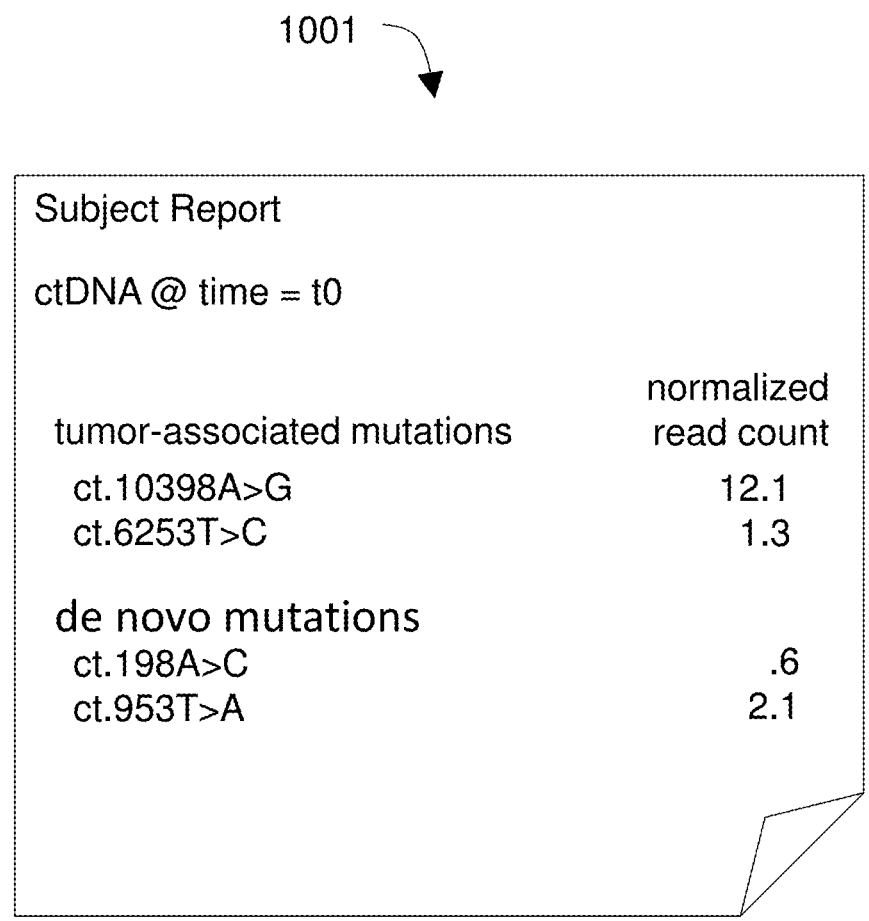
FIG. 10 illustrates a report of tumor-related mutations for a patient.

FIG. 10 illustrates a report of tumor-related mutations for a patient. The report 1001 preferably includes all known tumor-related mutations (if any) that reads are aligned to, along with any new de novo mutations identified. The report may show what proportion of reads aligned to each mutation branch, which counts may be normalized for total number of reads aligning at that position. The normalization step is recommended to correct for variation in coverage. Report 1001 is the patient's tumor-related mutation population at t0. The population of mutations can be understood as an initial assessment of clonality. Method of the invention may be used to monitor a tumor over time. For example, methods may be used to align a second set of sequence reads to the patient-specific genomic reference graph and produce a second report that identifies a patient's second tumor-related mutation population at a time different from an initial time associated with the patient's tumor-related mutation population.

The second report may include a comparison of the patient's second tumor-related mutation population to the patient's tumor-related mutation population.

FIG. 11 shows a report 1101 of patient mutations at a later point in time which may be deemed to be time=t1 (e.g., in the treatment scenario after treatment has had time to take effect; in the screening scenario after a reasonable time has passed such that screening again makes sense). A new set of reads from a newly-sequenced sample of the patient's cell-free plasma DNA is aligned to the patient-specific genomic reference graph. The alignment is used to report all tumor-related mutations that reads are aligned to together with proportion aligned. Thus report 1101 shows the patient's tumor-related mutation population at time=t1 along with a comparison of this population of mutations to the previous round of testing at time=t0. Any of the reports may identify a novel driver mutation present in the cell-free plasma DNA from the patient. Systems and methods of the invention may be used to add the novel driver mutation to the one or more known tumor-associated mutations in the patient-specific genomic reference graph for subsequent uses.

Figure 12:
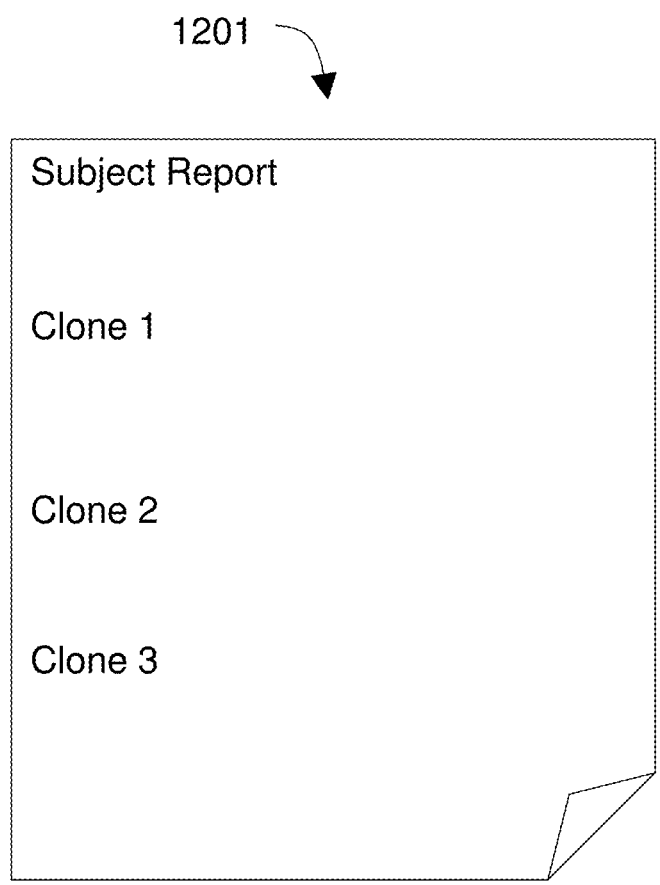
FIG. 12 shows a report describing tumor clones in a patient.

FIG. 12 shows a report describing the population of tumor clones present in a patient. It is understood that transformation and metastases are likely clonal in nature in that they derive from single cells. Indeed, identifying variants from a tumor provides the genotype of the founder cell. Numerous, tumor-associated driver mutations are known from sequencing and screening. A tumor genotype may be characterized by thousands of mutations, many of which are neutral. Data suggest that each tumor has an individually unique genomic profile. But prior attempts to profile tumor genotypes have provided only snapshots from a single time point. Sampling over time promises to allow tracking the evolution of a tumor. It has been suggested that patterns of segregation of mutations within sub-clones is lost when DNA is extracted from the total cell population. Systems and methods of the invention may allow for sub-clones to be properly reconstructed by mapping the cell-free plasma DNA reads to the patient-specific genomic reference graph and in essence haplotyping the results (e.g., as described in co-owned U.S. Provisional Application No. 62/165,403, filed May 22, 2015, and any patent or publication of that provisional, the contents of which are incorporated by reference in their entirety). Systems and methods of the invention may be used to provide reports that describe the clonal evolution of tumors, as well as specifically describing selectively advantageous or 'driver' lesions, selectively neutral or 'passenger' lesions, and deleterious lesions, as well as lesions that increase the rate of other genetic changes ('mutator' lesions). For additional background, see Greaves & Maley, 2012, Clonal evolution in cancer, Nature 481(7381):306-313, the contents of which are incorporated by reference for all purposes.

Discussed above are methods for analyzing tumor DNA using a patient-specific genomic reference graph. The invention also provides systems and methods for analyzing tumor DNA without using a patient-specific reference. The alternative non-patient-specific reference method may be preferable in some instances for being simpler in that it doesn't require whole-genome sequencing and more invasive sampling. The method for analyzing tumor DNA using a human reference DAG comprises the following steps:

1. building a human reference DAG comprising known reference genomes and known tumor-associated mutations;

2. obtaining sequence reads from a sequenced sample of a patient's cell-free plasma DNA and aligning the sequence reads to the human reference DAG; and 3. reporting one or more tumor-related mutations (preferably all) that the sequence reads align to, optionally with a proportion of reads aligned to that mutation branch (this may be taken as the patient's tumor-related mutation population at t0). The method may additionally include:

4. aligning—at a later point in time (e.g., in the treatment scenario after treatment has had time to take effect; in the screening scenario after a reasonable time has passed such that screening again makes sense)—a second set of sequence reads from a newly-sequenced sample of the patient's cell-free plasma DNA to the human reference DAG; and 5. reporting one or more (preferably all) known tumor-related mutations (if any) that sequence reads align to, preferably along with any de novo mutations identified, optionally with proportion aligned as in step 3 (which may be taken as the patient's tumor-related mutation population at t1) along with a comparison of this population of mutations to the previous round of testing.

Optionally, systems and methods of the invention may include variant calling 807 to describe de novo mutations from the ctDNA. The variant calling can include aligning sequence reads to the graph and reporting SNP alleles in a format such as a Sequence Alignment Map (SAM) or a Variant Call Format (VCF) file. Some background may be found in Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9): 1297-1303, the contents of each of which are incorporated by reference. Variant calling 831 produces results ("variant calls") that may be stored in a format similar to a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Additionally or alternatively, output from the variant calling may be provided in a format similar to a variant call format (VCF) file, e.g., in report 1201. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion may be found in U.S. Pub. 2013/0073214; U.S. Pub. 2013/0345066; U.S. Pub. 2013/0311106; U.S. Pub. 2013/0059740; U.S. Pub. 2012/0157322; U.S. Pub. 2015/0057946 and U.S. Pub. 2015/0056613, each incorporated by reference. Systems and methods of the invention may be used to describe and report a tumor-related mutation population or specific driver mutations as well as to profile changes over time.

Thus use of systems and methods of the invention provide a product that facilitates oncogenomics and patient counseling. A physician may use a report 1201 provided by the system to determine a medical course of action or counsel a patient on health and wellness issues.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing tumor DNA, the method comprising:
    obtaining a genomic reference graph that represents a plurality of known human genomic sequences, the genomic reference graph comprising a directed graph having vertices and edges stored as objects in a tangible memory subsystem of a computer system, wherein matching homologous portions of the sequences are each represented by a single object and portions that vary are represented as alternate objects, such that each of the plurality of known human genomic sequences is represented as a path in the genomic reference graph;
    creating a patient-specific genomic reference graph from the genomic reference graph, the creating comprising: aligning a first set of sequencing reads, obtained by sequencing a sample containing non-tumor DNA from the patient, to the genomic reference graph; identifying mutations relative to the genomic reference graph; and incorporating the identified mutations as alternate objects into the genomic reference graph to create the patient-specific genomic reference graph;
    aligning a second set of sequence reads, obtained by sequencing a sample containing cell-free plasma DNA from the patient, to the patient-specific genomic reference graph to find at least one mutation in the cell-free plasma DNA relative to the non-tumor DNA from the patient; and
    providing a report that circulating-tumor DNA (ctDNA) in the patient includes the at least one mutation found in the cell-free plasma DNA.

2. The method of claim 1, wherein the report identifies a patient's tumor-related mutation population, wherein the tumor-related mutation population includes all mutations in the cell-free plasma DNA relative to the non-tumor DNA from the patient.

3. The method of claim 2, wherein the genomic reference graph is annotated to describe one or more known tumor-associated mutations, and the report further includes what portion of the second set of sequence reads align to mutation-associated branches in the patient-specific genomic reference graph.

4. The method of claim 2, wherein the report identifies a first clone and a second clone present in a tumor in the patient.

5. The method of claim 2, wherein the report identifies a driver mutation not present in the known human genomic sequences and present in the cell-free plasma DNA from the patient.

6. The method of claim 5, further comprising adding the driver mutation as a known tumor-associated mutation in the patient-specific genomic reference graph for subsequent uses.

7. The method of claim 2, further comprising building the genomic reference graph by:
    obtaining the known human genomic sequences;
    finding matching homologous portions among the known human genomic sequences;
    creating one of the objects in the tangible memory subsystem for each of the matching homologous portions; and
    creating connections between pairs of the objects to create the genomic reference graph.

8. The method of claim 7, further comprising aligning a third set of sequence reads to the patient-specific genomic reference graph and producing a second report that identifies a patient's second tumor-related mutation population at a time different from an initial time associated with the patient's tumor-related mutation population, wherein the second report includes a comparison of the patient's second tumor-related mutation population to the patient's tumor-related mutation population.

9. The method of claim 7, wherein the objects of the patient-specific genomic reference graph include pointers to adjacent ones of the objects such that the objects are linked into paths to represent the plurality of known human genomic sequences, wherein each pointer identifies a physical location in the memory subsystem at which the adjacent object is stored.

10. The method of claim 9, further comprising obtaining the second set of sequence reads by sequencing the sample containing the cell-free plasma DNA from the patient.

11. A system for analyzing tumor DNA, the system comprising a processor coupled to a memory subsystem having stored therein:
    a genomic reference graph representing a plurality of known human genomic sequences, the genomic reference graph comprising a directed graph having vertices and edges stored as objects, wherein matching homologous portions of the sequences are each represented by a single object and portions that vary are represented as alternate objects, such that each of the plurality of known human genomic sequences is represented as a path in the genomic reference graph, the objects stored in the memory subsystem; and
    instructions executable by the processor to cause the system to:
        create a patient-specific genomic reference graph from the genomic reference graph, the creating comprising: aligning a first set of sequence reads, obtained by sequencing a sample containing non-tumor DNA from the patient, to the genomic reference graph; identifying mutations relative to the genomic reference graph; and incorporating the identified mutations as alternate objects into the genomic reference graph to create the patient-specific genomic reference graph;
        align a second set of sequence reads from cell-free plasma DNA of the patient to the patient-specific genomic reference graph to find at least one mutation in the cell-free plasma DNA relative to the non-tumor DNA from the patient; and
        provide a report that circulating-tumor DNA (ctDNA) in the patient includes the at least one mutation found in the cell-free plasma DNA.

12. The system of claim 11, wherein the report identifies a patient's tumor-related mutation population, wherein the tumor-related mutation population includes all mutations in the cell-free plasma DNA relative to the non-tumor DNA from the patient.

13. The system of claim 12, wherein the genomic reference graph is annotated to describe one or more known tumor-associated mutations, and the report further includes what portion of the second set of sequence reads align to mutation-associated branches in the patient-specific genomic reference graph.

14. The system of claim 12, wherein the report identifies a first clone and a second clone present in a tumor in the patient.

15. The system of claim 12, wherein the report identifies a driver mutation not present in the known human genomic sequences and present in the cell-free plasma DNA from the patient.

16. The system of claim 15, further operable to add the driver mutation as a known tumor-associated mutation in the patient-specific genomic reference graph for subsequent uses.

17. The system of claim 12, further operable to build the genomic reference graph by:
 obtaining the known human genomic sequences;
 finding matching homologous portions among the known human genomic sequences;
 creating one of the objects in the tangible memory subsystem for each of the matching homologous portions; and
 creating connections between pairs of the objects to create the genomic reference graph.

18. The system of claim 17, further operable to align a third set of sequence reads to the patient-specific genomic reference graph and produce a second report that identifies a patient's tumor-related mutation population at a time different from an initial time associated with the patient's tumor-related mutation population, wherein the second report includes a comparison of the patient's second tumor-related mutation population to the patient's tumor-related mutation population.

19. The system of claim 17, wherein the objects of the patient-specific genomic reference graph include pointers to adjacent ones of the objects such that the objects are linked into paths to represent the plurality of known human genomic sequences, wherein each pointer identifies a physical location in the memory subsystem at which the adjacent object is stored.

20. The system of claim 17, further comprising a nucleic acid sequencing instrument, the system further operable to obtain the second set of sequence reads by sequencing the sample containing the cell-free plasma DNA from the patient using the nucleic acid sequencing instrument.

* * * * *